United States Patent [19]

Cisney et al.

[11] 4,089,904

[45] May 16, 1978

[54] PROCESS FOR SELECTIVELY PRODUCING HIGH-YIELD, HIGH-PURITY 4,4-SUBSTITUTED DIARYL SULFONES

[75] Inventors: Merle E. Cisney; Neil J. Lasater, both of Camas, Wash.

[73] Assignee: Crown Zellerbach Corporation, San Francisco, Calif.

[21] Appl. No.: 567,350

[22] Filed: Apr. 11, 1975

[51] Int. Cl.² .............................................. C07C 147/06
[52] U.S. Cl. ........................ 260/607 AR; 260/607 E;
[58] Field of Search ...................... 260/607 AR, 607 O

[56] References Cited

U.S. PATENT DOCUMENTS

| 2,560,049 | 7/1951 | Cook | 260/607 AR |
| 2,560,050 | 7/1951 | Cook | 260/607 AR |
| 3,005,852 | 10/1961 | Freyermuth et al. | 260/607 AR |
| 3,006,962 | 10/1961 | Schultz et al. | 260/607 AR |

OTHER PUBLICATIONS

Schultz; J. Org. Chem., vol. 28, pp. 1140–1142, (1962).

Primary Examiner—Delbert R. Phillips
Attorney, Agent, or Firm—Jerome S. Marger; Corwin R. Horton

[57] ABSTRACT 4,4'-substituted diaryl sulfones of high yield and high purity are selectively formed by the oxidation of 4,4'-substituted diaryl sulfides and diaryl sulfoxides, respectively, employing an aqueous slurry, including a molybdic acid-peroxide-catalyzed oxidation system, the aqueous slurry being maintained at a pH of less than about one.

16 Claims, No Drawings

PROCESS FOR SELECTIVELY PRODUCING HIGH-YIELD, HIGH-PURITY 4,4-SUBSTITUTED DIARYL SULFONES

BACKGROUND OF THE INVENTION

Various methods have been proposed by the prior art for the production of sulfones. The best known prior art processes for producing sulfones is probably the reaction of two moles of phenol with one mole of sulfuric acid to form a sulfone compound and water. Unfortunately, a major drawback to this method is that a substantial amount (10–29%) of the 2,4'-isomer by-product, instead of the desired 4,4'-isomer product, is provided when the above process is employed. And, since the removal of the 2,4'-isomer from the product mixture is difficult, additional losses of 4,4'-isomer result during purification. Therefore, the final yield of product is relatively low. Furthermore, dark-colored impurities and tars are formed which are also difficult to eliminate. Finally, the disposal of both of the above impurities provides ecological problems to the manufacturer.

U.S. Pat. No. 3,297,766 to Bradley et al.; 3,318,956 to Mausner; 3,366,692 to Orem; and 3,383,421 to Fox et al., describe various schemes to produce a high-purity sulfone employing the above phenol-sulfuric acid reaction.

Another process is U.S. Pat. No. 3,699,171 to Sanderson et al., which provides a process employing nitrogen oxide in the presence of sulfuric acid and a molecular oxygen to produce an aryl alkyl sulfone from an aryl alkyl sulfoxide. Moreover, U.S. Pat. Nos. 2,793,234 to Metivier; 3,019,266 to Buc et al.; 3,069,471 to Tashlick; 3,118,952 to Crowther et al., all provide methods employing peroxide to oxidize alkyl or dialkyl sulfides and/or sulfoxides to their corresponding sulfone compounds.

In U.S. Pat. No. 3,449,439 to Kuhnen et al., a sulfone is produced from an organic sulfide, or organic sulfoxide, by reacting same with an organic hydroperoxide in the presence of a metallic catalyst compound of titanium, molybdenum, or vanadium.

Three patents assigned to General Aniline and Film Corporation, U.S. Pat. Nos. 3,005,852 to Freyermuth; 3,006,962 to Schultz et al.; and 3,006,963 to Buc et al., describe the production of sulfoxides and sulfones by an oxidation process employing as a catalyst system hydrogen peroxide and a molybdenum, vanadium, or tungsten catalyst. In each case, a two-stage reaction sequence is provided. In stage one, the sulfide is oxidized to sulfoxide, while in the second stage, the sulfoxide is converted oxidatively to the sulfone. "Cooling is often required to prevent the temperature from rising to a point detrimental to the reaction or to the chemical structure of the intermediate and final compound." (see U.S. Pat. No. 3,005,852, page 2, column 3).

For instance, in the Freyermuth et al. patent, a molybdenum-peroxide catalyst is provided to oxidize a dialkyl sulfide compound. More specifically, the dialkyl compound comprises a single aromatic ring structure attached to the terminal alkyl group of at least one pendant constituent having a structure in which a divalent sulfur atom is attached to a pair of alkyl groups. The compound, for purpose of the sulfide oxidation, acts as a dialkyl, not a diaryl, sulfide. The broad pH range over which the subject reaction is supposedly viable is from about one to about 10 to 11, preferably pH range being from 5 to 7. It is noted, however, that all of the reactions shown in the examples in this application are run at a pH of 5 to 6.

Next, in the Schultz et al. patent, the vanadium-peroxide catalyst is employed to oxidize a reactant compound containing at least one divalent sulfur atom bonded to two carbon atoms, although no diaryl sulfide reactants are shown in the examples. The broadest pH range in this case is from 0.5 to 6, the preferable range being from about 1 to 3.

Finally, the Buc et al. patent presents a tungsten-peroxide oxidation system in which a divalent sulfur atom bonded to two carbon atoms is reacted to form a sulfoxide or a sulfone, the pH range being from about one to 10 or 11, and preferably from about 6 to 7.

It is quite clear from reviewing the above patents that different reactants at different pH levels are provided in each of the various catalyst systems employed in each of the three patents set forth. Accordingly, the above differences among oxidation catalyst systems preclude extrapolation of the reaction parameters outlined for a given catalyst with respect to another catalyst. Instead, the differences limit each reaction system to include only the reactants and process conditions which they particularly disclose and specify. As an illustration in support of the proposition that each of the above GAF patents is self-limiting, an article in the Journal of Organic Chemistry, Volume 28, pages 1140–1142, (1963), the above patentees, i.e., Freyermuth, Schultz and Buc, have co-authored an article entitled "New Catalysts for the Oxidation of Sulfides to Sulfones with Hydrogen Peroxide". On page 1141 of the above article, the authors state, in the first sentence of column 1, paragraph 2, that "The vanadium catalyst is satisfactory only in the pH range 1–2." Furthermore, in the first sentence of column 1, paragraph 3, statement is made that "Tungsten and molybdenum catalysts are operable over a broader pH range than the vanadium catalyst. The preferred pH is about 5–6, but satisfactory reactions have been carried out at about pH 3–8."

Finally, an article entitled "Catalysts for the Hydrogen Peroxide Oxidation of Sulfides to Sulfones", by N. W. Connon, Eastman Organic Chemical Bulletin, Volume 44, No. 1 (1972), provides a review of the prior art including a number of the references cited above. The Eastman bulletin discloses the oxidation of water-soluble di-aliphatic sulfides, employing molybdate salts as catalysts for the hydrogen peroxide in that oxidation.

SUMMARY OF THE INVENTION

A process is provided herein for selectively forming a high-purity, light-colored 4,4'-substituted diaryl sulfone product, in a yield of at least 90% by weight, and preferably 95% by weight, based on the total weight of 4,4'-substituted diaryl sulfone product recovered, while producing only a minimal amount of undesirable by-products, i.e., 4,4'-substituted diaryl sulfoxides, 2,4'-substituted diaryl sulfones, and the like. With respect to color, the 4,4'-substituted diaryl sulfone product has an absorbence of not more than 0.5, and preferably not more than 0.35, absorbence unit, as measured on a 25% solution of the sulfone product by weight in methanol, at a wave length of 450 n.m. The process entails reacting, in a highly acidic, aqueous slurry, a diaryl reactant compound selected from the group consisting of diaryl sulfides and diaryl sulfoxides, an oxidizing agent, and a catalyst compound selected from the group consisting of molybdic acid and salts thereof. The level of acidity of the aqueous slurry is maintained at a pH less than one.

By employing the above process, several totally unexpected results occur. First, a substantially water-white 4,4'-substituted diaryl sulfone product is formed having a high degree of purity, i.e, the weight percent of 4,4'-isomer in the reaction product. More specifically, the sulfone product is preferably formed at a purity of at least about 96% and more preferably at a purity of at least 98%. The conversion to 4,4'-substituted diaryl sulfone product is calculated by dividing the actual amount of product recovered by the amount of 4,4'-substituted diaryl sulfone product which should theoretically be formed, the entire quotient then being multiplied by 100. Preferably, a conversion of at least about 96% is provided. Yield is determined by multiplying conversion times purity, and dividing by 100.

The combination of high yield and excellent color, as well as high purity and high conversion, is completely unexpected and unforeseeable since, as opposed to dialkyl sulfide and sulfoxide reactants, their diaryl counterparts, and more particularly their hydroxy-substituted diaryl sulfone counterparts, are susceptible to the formation of colored bodies (chromophores) during the oxidation process due to the presence of a substantial number of conjugated double bonds. As will hereinafter be demonstrated, in the accompanying examples, only when the pH of the aqueous slurry is maintained below a value of one is both the formation of a light-colored product as well as high yields of the 4,4'-substituted diaryl sulfone simultaneously provided. Moreover, the amount of 4,4'-substituted diaryl sulfoxide by-product is preferably less than about 1.5% by weight and, more preferably, less than about 0.5% by weight, based on the weight of total product formed. The formation of a minimal amount of the sulfoxide is important since, as in the case of 2,4'-isomer, removal thereof is quite difficult.

This combination of light-colored, high purity and high yield is in complete contradistinction to any teachings of the prior art.

DETAILED DESCRIPTION OF THE PREFERRED EMBODIMENTS

The 4,4'-substituted diaryl reactant compounds, as defined for purposes of this invention, are selected from a group consisting of 4,4'-substituted diaryl sulfides and 4,4'-substituted diaryl sulfoxides. More specifically, exemplary reactant compounds for use in the subject process include, but are not limited to, the following structural formula:

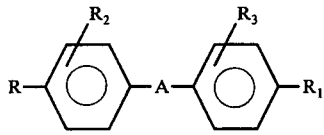

wherein A is sulfide or sulfoxide, R and $R_1$ are OH, halogen, hydrogen, alkyl, or alkoxy, and $R_2$ and $R_3$ are H, halogen, or an alkyl group having from one to three carbon atoms. Illustrative of the 4,4'-substituted diaryl reactant compound employed herein are any or all of the following:
4,4'-thiodiphenol, 4,4'-thiodianisole, diphenyl sulfide, bis(4-chlorophenyl sulfide), the 4,4'-thiodicresols, or the corresponding sulfoxides thereof.

The second component of the subject aqueous reactant slurry is an oxidizing agent. The oxidizing agent employed is generally a peroxide compound, and due to the low cost and abundant availability thereof, is preferably hydrogen peroxide. However, other compounds, such as peracidic acid, persulfuric acid, and the like, may also be employed. Although stoichiometric amounts of peroxide can be provided for use herein, the amount in excess of stoichiometric is preferred.

A catalyst compound is also included in the aqueous reactant slurry of the present invention, and is selected from the group consisting of molybdic acid and salts thereof. The catalyst compound employed is effective at a level of from about 0.001 mole percent, and preferably from about 0.01 mole percent, and more preferably from about 0.1 mole percent, up to about 5.0 moles percent, and preferably up to about 1.0 mole percent, and more preferably up to about 0.5 mole percent, based on the moles of 4,4'-substituted diaryl compound employed.

The aqueous slurry is made highly acidic by the addition of a strong mineral acid thereto. Preferably, the mineral acid is sulfuric acid. As opposed to the prior art GAF patents which require pH control within a specified range approaching neutrality, which is rather difficult to accomplish on a large-scale scale basis, generally requiring the use of buffering agents and the like, the pH of the subject slurry can be easily maintained below a pH of one, and preferably at a pH of not more than about 0.7. As an illustration, in order to maintain the reaction at the requisite pH level for forming the subject sulfone product, the acidity of the aqueous slurry, calculated on the basis of the hydrogen ion concentration in grams per liter, is from greater than about 0.1, and preferably greater than about 0.2. A preferred upper level of acidity, based on considerations such as cost, contemplates a hydrogen ion concentration of up to about 2.5 grams per liter of strong mineral acid, and more preferably up to about 2.0 grams per liter.

Although the novel process of this invention may be conducted quite readily in a batch or semibatch system, it is a preferred embodiment of this invention that the reaction herein be selectively conducted by continuously combining the reactant, oxidizing agent, and catalyst, respectively, in the highly acidic, aqueous slurry while, at the same time, continuously drawing off the 4,4'-diarly sulfone product being formed.

The aqueous slurry of the present invention can be readily provided at any concentration which permits adequate intermixing of the respective components one with the other. More specifically, concentration of the diaryl reactant compound in the aqueous slurry is preferably employed at about a 0.5 weight percent, and more preferably at about a 1% by weight level, based on the total weight of the slurry, and up to an amount at which effective intermixing cannot be provided, and more preferably up to about 50% by weight of the diaryl compound.

The pressure in the reactor during the sulfone formation process of the present invention, based on economic considerations, is generally maintained at an atmospheric level. However, superatmospheric pressures may be employed.

The reaction temperture employed, contrary to the prior art GAF patents, does not have to be controled by a cooling period. In fact, for optimum results, the reaction should be at temperature of at least about 80° C., and preferably at least about 90° C., up to the boiling point temperature of the aqueous reaction slurry. However, for ease of operation, the reaction should be conducted at or near the boiling point temperature.

The high-yield, light-colored diaryl sulfone product of the present invention is prepared employing an aqueous reaction slurry having as its components water, a diaryl compound, an oxidizing agent, and a catalyst compound. Preferably, a one-stage process, as opposed to the two-stage methods of GAF, is provided in which a 4,4'-substituted diaryl compound is selectively oxidized, in a direct manner, to the sulfone without requiring the isolation of a 4,4'-substituted sulfoxide intermediate, thus eliminating the need for a two-stage reaction sequence. In this preferred case, the subject reaction is conducted by adding the 4,4'-substituted diaryl reactant compound, over a relatively short period of time, to an aqueous solution including the oxidizing agent and catalyst compound. More specifically, a preferred reaction time of not more than about 1 hour, and more preferably not more than about one-half hour can be provided by the process of this invention.

EXAMPLE 1

A 3-neck, round-bottom flask was equipped with a stirrer, thermometer, reflux condenser and with an opening for the introduction of solid 4,4'-thiodiphenol. A solution was prepared by adding to 740 cc of water, 18.4 grams (0.188 mole) of sulfuric acid. The hydrogen ion concentration was calculated to be 0.5 g/l. 149.6 grams (2.2 moles) of 50% aqueous hydrogen peroxide and 1.5 grams of sodium molybdate (dihydrate) were then introduced into the flask and resulting solution heated to boiling (about 101°–102° C.). Over about a one-half hour time period, 218 grams (1.0 mole) of the 4,4'-thiodiphenol were added. When the addition of thiodiphenol was complete, the slurry was heated for about an additional one-half hour, cooled, filtered, and the cooled product washed with about 400–500 cc of water in small portions. The resultant product was dried and found to weigh 244.8 grams. The material was light-colored, having an absorbence of 0.25 absorbence units, as measured on a 25% solution by weight of the product in methanol, at a wave length of 450 n.m. on a Perkin-Elmer 402 UV-visible Spectrophotometer. Analysis of the product showed a purity of 99.5% 4,4'-sulfonyldiphenol, 0.3% 4,4'-sulfinyldiphenol, and about 0.2% of unknown contaminants. The yield of 4,4'-sulfonyldiphenol product was calculated to be 97.6%.

Therefore, by employing the process of this invention, a high-purity (99.5%), light-colored (absorbence = 0.25), high-yield (97.6%), high-conversion (98.1%) 4,4'-sulfonyldiphenol product, containing substantially no 2,4'-sulfonyldiphenol by-product, can be provided.

EXAMPLE 2

The process described in Example 1 of U.S. Pat. No. 3,005,852 to Freyermuth was repeated, using a diaryl sulfide compound (4,4'-thiodiphenol). The following results were obtained:

(A) Conversion = 92.1%

(B) Purity = 92.8%

(C) Yield = 85.5%

(D) Absorbence = greater than 1.5 absorbence units (the maximum reading attainable on instrument is 1.5 absorbence units)

(E) Color = tan (dark)

(F) Amount of 4,4'-sulfinyldiphenol = 7.2%

It is clear from observing the above results that the requisite conversion, purity, yield, color, absorbence, and percent sulfoxide parameters provided in the process of the subject invention cannot be obtained by surreptitiously interposing a diaryl sulfide compound into the process of Freyermuth et al. because it was, in fact, designed only for the oxidation of dialkyl sulfides to either the dialkyl sulfoxide or sulfone.

EXAMPLE 3

The process of the present invention was employed using the acidity parameter specifically described in the examples of U.S. Pat. No. 3,005,852 to Freyermuth et al., namely, a pH of 5. This was accomplished employing the process of the present invention as described in Example 1 above, the difference in the pH of the respective experiments, i.e., a pH of 0.7 vs. a pH of 5, being the only difference between Examples 1 and 3, respectively. The results of this latter run are as follows:

(A) Conversion = 89.5%

(B) Purity = 92.5%

(C) Yield = 82.6%

(D) Absorbence = greater than 1.5 absorbence units (E) Color = brown solid (very dark)

(F) 4,4'-sulfinyldiphenol content = 4.3%

It is again clear from observing the results of this latter run (pH of 5) that the critical parameters of conversion, purity, yield, absorbence, color, and sulfoxide content were again below the required levels set forth in the subject application for the product produced by the process of this invention.

EXAMPLE 4

The table shown below indicates varying acidity levels based on sulfuric acid of the aqueous slurry employed in the formation of the requisite 4,4'-substituted diaryl sulfone product. Concentration and normality of each run is compared using color and yield as the criteria for determining the acceptability of a given 4,4'-substituted diaryl sulfone product.

| Run No. | Normality (gram-equivalents per l.) | Hydrogen Ion Concentration (grams per l.) | Yield | Color |
|---|---|---|---|---|
| A | $1 \times 10^{-5}$ | $0.5 \times 10^{-5}$ | 82.6% | >1.5 |
| B | 0.2 | 0.1 | 94.3% | 1.05 |
| C | 0.5 | 0.27 | 97.6% | 0.25 |
| D | 2.0 | 1.0 | 96.0% | 0.22 |
| E | 2.5 | 1.25 | 97.6% | 0.33 |

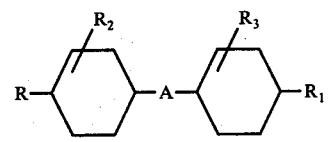

EXAMPLE 5

In the following experiments, two different 4,4'-substituted diaryl reactant compounds were employed in the process outlined in Example 1 to form 4,4'-substituted diaryl compounds.

In the first instance, diphenyl sulfide was oxidized in a similar manner to the procedure described in Example 1. The resultant product exhibited a conversion of 96.2%, a purity of 98.8%, a yield of 95.0%, and absorbence of less than 0.30 absorbence units, and a water-white color.

In another experiment, 4,4'-thiodianisole was reacted in a manner similar to the procedure outlined in Example 1, the resultant 4,4'-substituted diaryl sulfone compound having a conversion of 99.2%, a purity of 96.2%, a yield of 95.5%, an absorbence of less than 0.3 absorbence units, and a water-white color.

EXAMPLE 6

In U.S. Pat. No. 3,066,962 to Schultz et al., a vanadium-peroxide catalyst system is employed, the reaction medium being maintained at a pH ranging from about 0.5 to 6 and, preferably, 1 to 3. Thus, the procedure described in Example 1 herein was again repeated, using two vanadium salts as the catalysts compound.

In the first case, a vanadyl sulfate catalyst produced a brown, lumpy material at a yield of less than 70%, having an absorbency which was measured at greater that 1.5 absorbence units.

In the second instance, a sodium vanadate catalyst was employed. The product formed was a brown, oily tar, formed at a yield of less than 60%, and again having an absorbency of greater than 1.5 absorbence units.

Clearly, even though a pH range of 0.5 to 6 is broadly disclosed herein for producing sulfoxide- and sulfone-containing compounds employing a vanadium compound as the catalyst, the prior art vanadium catalyst cannot be employed in the process of the present invention.

The terms and expressions which have been employed in the foregoing abstract, specification, and examples, have been provided herein for purposes of description and not of limitation, and there is no intention in their use of excluding equivalents thereof, it being recognized that the scope of the invention is defined and limited only by the claims which follow.

We claim:

1. A process for selectively forming a high-purity, light-colored 4,4'-substituted diaryl sulfone product, having an absorbency of not more than about 0.50 absorbence units, as measured on a 25% solution by weight in methanol of said sulfone product at a wave length of 450 n.m., and having a yield of at least 90% by weight, which comprises reacting, in a highly acidic, aqueous slurry, a 4,4'-substituted diaryl reactant compound comprising the structural formula

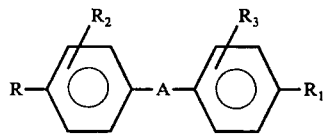

wherein A is sulfide or sulfoxide, R and $R_1$ are OH, halogen, H, alkoxy, or alkyl, and $R_2$ and $R_3$ are H, halogen, or an alkyl group having from one to three carbon atoms, an oxidizing agent comprising a peroxide compound, and a catalyst compound selected from the group consisting of molybdic acid and a salt thereof, the level of acidity of said aqueous slurry being maintained at a pH of less than one.

2. The process of claim 1, wherein the acidity level of said aqueous slurry is maintained at a pH of not more than about 0.7.

3. The process of claim 1, wherein the absorbence of said 4,4'-substituted diaryl sulfone product is not more than about 0.35 absorbence units.

4. The process of claim 1, wherein the purity of the 4,4'-substituted diaryl sulfone product is at least about 98%.

5. The process of claim 1, wherein the conversion of the 4,4'-substituted diaryl reactant compound is at least 96% by weight.

6. The process of claim 1, wherein the yield of said 4,4'-substituted diaryl sulfone product is at least about 95%.

7. The process of claim 1, wherein the amount of 4,4'-substituted diaryl sulfoxide produced during said selective formation process is less than about 1.5.

8. The process of claim 1, wherein the 4,4'-substituted diaryl sulfone product is 4,4'-sulfonyldiphenol, and the 4,4'-substituted diaryl sulfide reactant compound is 4,4'-thiodiphenol.

9. The process of claim 1, wherein the amount of 2,4'-sulfonyldiphenol by-product formed is less than about 0.5% by weight, based on the total weight of recovered product.

10. The process of claim 1, wherein the level of acidity in the aqueous slurry, based on the hydrogen ion concentration, is more than about 0.1 gram per liter.

11. The process of claim 10, wherein the hydrogen ion concentration of the aqueous slurry is at least 0.2 gram per liter.

12. The process of claim 1, wherein the 4,4'-substituted diaryl reactant compound is selected from the group consisting of 4,4'-thiodiphenol, 4,4'-thiodianisole, diphenyl sulfide, and the sulfoxides thereof.

13. The process of claim 1, wherein the reaction temperature is at least about 80° C., up to the boiling point of the aqueous slurry.

14. The process of claim 1, wherein the oxidizing agent is selected from the group consisting of hydrogen peroxide, persulfuric acid and peracetic acid.

15. A process for selectively forming a high-purity 4,4'-substituted diaryl sulfone product, having an absorbency of not more than about 0.50 absorbence units, as measured on a 25% by weight solution of said 4,4'-substituted product in methanol at a wave length of about 450 n.m., and having a yield of at least about 90% by weight, which comprises (a) forming a highly acidic, aqueous solution including an oxidizing agent comprising a peroxide compound, a catalyst compound selected from the group consisting of molybdic acid and a salt thereof, the aqueous solution being maintained at a pH of less than one;

(b) adding a 4,4'-substituted diaryl reactant compound comprising the structural formula

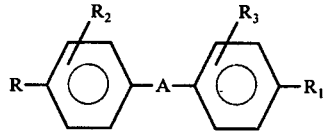

wherein A is sulfide or sulfoxide, R and $R_1$ are OH, halogen, H, alkyl, or alkoxy, and $R_2$ and $R_3$ are H, halogen, or an alkyl group having from one to three carbon atoms, to said solution to form a highly acidic, aqueous slurry; and (c) oxidizing said 4,4'-substituted diaryl reactant compound in said slurry to produce said 4,4'-substituted diaryl sulfone product.

16. The process of claim 15, wherein the 4,4'-substituted diaryl reactant compound is selected from the group consisting of 4,4'-thiodiphenol, 4,4'-thiodianisole, diphenyl sulfide, and the sulfoxides thereof.

* * * * *